United States Patent [19]

Furrer et al.

[11] 4,284,797

[45] Aug. 18, 1981

[54] PROCESS FOR SEPARATING MIXTURES OF 3- AND 4-NITROPHTHALIC ACID

[75] Inventors: Peter Furrer, Bottmingen; Harry Beyeler, Basel, both of Switzerland

[73] Assignee: Ciba-Geigy Corporation, Ardsley, N.Y.

[21] Appl. No.: 44,122

[22] Filed: May 31, 1979

[30] Foreign Application Priority Data

Jun. 5, 1978 [CH] Switzerland .................... 6135/78

[51] Int. Cl.$^3$ .............................................. C07C 79/46
[52] U.S. Cl. .................................................. 562/434
[58] Field of Search ......................................... 562/434

[56] References Cited

U.S. PATENT DOCUMENTS

1,549,885   8/1925   Littmann .............................. 562/434

FOREIGN PATENT DOCUMENTS

| | | |
|---|---|---|
| 824815 | 7/1949 | Fed. Rep. of Germany . |
| 935964 | 12/1955 | Fed. Rep. of Germany . |
| 936944 | 12/1955 | Fed. Rep. of Germany . |
| 1224731 | 9/1966 | Fed. Rep. of Germany ............ 562/434 |
| 374010 | 5/1932 | United Kingdom . |
| 427251 | 4/1935 | United Kingdom ..................... 562/434 |
| 736974 | 9/1955 | United Kingdom . |
| 1165637 | 10/1969 | United Kingdom . |

OTHER PUBLICATIONS

Hine, Physical Organic Chemistry, pp. 81–103 (1962).

*Primary Examiner*—Robert Gerstl
*Attorney, Agent, or Firm*—Michael W. Glynn

[57] ABSTRACT

A novel improved process for separating mixtures of 3- and 4-nitrophthalic acid is described. The said process comprises treating a mixture of 3- and 4-nitrophthalic acid, which mixture is free from inorganic acid residues, in an aqueous-organic medium containing 1–20 percent by volume of water, at a temperature of between 20° and 100° C., stepwise with a base capable of forming salts of 3- and 4-nitrophthalic acid, which salts are essentially insoluble in the reaction medium, the treatment being carried out by adding base until a pH value of about 2.8 is obtained, separating the precipitating product consisting mainly of a 3-nitrophthalic acid monosalt, subsequently precipitating, by the addition of further base, a product consisting principally of a 4-nitrophthalic acid salt, and finally converting the resulting nitrophthalic acid salts separately into the corresponding free acids, and optionally purifying these. The 3- and 4-nitrophthalic acid can be obtained by the process according to the invention in a simple manner in an isomer-free form and in good to very good yields.

9 Claims, No Drawings

PROCESS FOR SEPARATING MIXTURES OF 3- AND 4-NITROPHTHALIC ACID

The present invention relates to a novel process for separating mixtures of 3- and 4-nitrophthalic acid.

3- and 4-Nitrophthalic acids are commercially valuable intermediates for producing the widest variety of derivatives, such as pigments, dyes and plasticisers, particularly for PVC, polyesters, polyamides, peptides, agricultural active substances, and so forth [see, for example German Patent Specifications Nos. 824,815, 935,964 and 936,944; U.S. Patent Nos. 2,412,817 and 2,491,455; CA, 47,9303d (1953), 53,11290f (1959), 66,116023b (1967), 69,107329r and 170330i (1968)]. They are in general produced by nitration of phthalic anhydride with concentrated sulfuric acid. There are formed by this method isomeric mixtures having varying proportions of 3- and 4-nitrophthalic acid.

The processes known hitherto for separating isomeric mixtures of aromatic polycarboxylic acids are in some cases complicated and unsuitable for carrying out on a large commercial scale, such as chromatographical methods, or they do not enable a clean separation into the desired isomers to be effected.

According to U.S. Pat. No. 2,412,817, mixtures of 3- and 4-nitrophthalic acid can be separated by suspension and stirring in water at room temperature, and filtering off the 3-nitrophthalic acid present in the undissolved state. 3-Nitrophthalic acid does indeed have a lower solubility in water than does 4-nitrophthalic acid, but in no way is it insoluble in water. Accordingly, no clean separation into the pure isomers is possible by this method.

In the U.S. Pat. No. 3,098,095 there is described a process for separating mixtures of anhydride-forming aromatic polycarboxylic acids of which at least one contains a further ring substituent, inter alia mixtures of 3- and 4-nitrophthalic acid. In this process the acid mixture is heated in a suitable solvent to the temperature at which principally the anhydride of the carboxylic acid with the lowest dehydration temperature is formed, whilst the dehydration rate of the other carboxylic acid(s) is kept as low as possible. The fractions enriched with anhydride and acid, respectively, are subsequently separated, for example by means of solvent extraction of the fraction enriched with anhydride. Also this process is not suitable for large-scale commercial production of pure isomers, because there are also obtained considerable proportions of the anhydride of the carboxylic acid(s) having a higher dehydration temperature range. Thus, for example, in the case of the 3- and 4-nitrophthalic acid, the fraction enriched with anhydride contains, besides the main proportion of 4-nitrophthalic anhydride, also about 8.5% of 3-nitrophthalic anhydride. Furthermore, the reaction generally has to be performed at elevated temperatures (about 110°–180° C.) and in highly diluted systems, factors which impair the economical efficiency of this process.

It was therefore the object of the present invention to provide a novel process which enables mixtures of 3- and 4-nitrophthalic acid to be cleanly separated into the individual isomers in a simple and economical manner and with high yields, and which moreover is suitable for a large-scale commercial application.

The process according to the invention for separating mixtures of 3- and 4-nitrophthalic acid comprises treating a mixture of 3- and 4-nitrophthalic acid, which is free from inorganic acid residues, in an aqueous-organic medium containing 1–20, and preferably 5–10, percent by volume of water, at a temperature of between 20° and 100° C., stepwise with a base capable of forming salts of 3- and 4-nitrophthalic acid, which salts are essentially insoluble in the reaction medium, the treatment being carried out by adding base until a pH value of about 2.8 is obtained, separating the precipitating product consisting mainly of a 3-nitrophthalic acid mono-salt, subsequently precipitating by the addition of further base a product consisting principally of a 4-nitrophthalic acid salt, and finally converting the resulting nitrophthalic acid salts separately into the corresponding free acids, and optionally purifying these.

The organic solvents used in the process according to the invention are advantageously inert polar organic solvents, particularly those able to dissolve at room temperature a certain, but limited, amount of water. Examples of suitable solvents are: aliphatic and cycloaliphatic ketones, such as acetone, methyl ethyl ketone, cyclopentanone and cyclohexanone; cyclic ethers, such as tetrahydrofuran, tetrahydropyran and dioxane; cyclic amides, such as N-methyl-2-pyrrolidone, N-acetyl-2-pyrrolidone and N-methyl-ε-caprolactam; ethylene glycol mono- and -dialkyl ethers having 1–4 C atoms in each of the alkyl moieties, such as ethylene glycol monomethyl ether, ethylene glycol monoethyl ether, ethylene glycol monoisopropyl ether and ethylene glycol mono-n-butyl ether, ethylene glycol dimethyl ether and ethylene glycol diethyl ether; alkyl esters of aliphatic monocarboxylic acids having a total of 2–6 C atoms, such as formic or acetic acid methyl ester, formic or acetic acid ethyl ester and formic or acetic acid-n-butyl ester; and aliphatic alcohols having 1–6 C atoms, such as methanol, ethanol, propanol, isopropanol, butanols and pentanols.

Preferred solvents are alkyl esters and aliphatic ketones of the aforementioned type, especially acetic acid ethyl ester and methyl ethyl ketone.

It is possible to use as bases in the process of the invention any organic or inorganic compounds capable of forming with the 3- and 4-nitrophthalic acid in the reaction medium difficultly-soluble and insoluble salts, respectively. Inorganic bases are preferably used, particularly hydroxides, carbonates and hydrogen carbonates of alkali metals and alkaline-earth metals, such as hydroxides, carbonates or hydrogen carbonates of sodium, potassium, magnesium and calcium. Sodium hydrogen carbonate and potassium hydrogen carbonate are especially preferred.

The reaction temperatures for the formation of salts are advantageously between about 30° and 50° C.

As defined, base is added in the first stage of the process until a pH value of about 2.8 is obtained, in the course of which there is formed principally a 3-nitrophthalic acid mono-salt which can still contain traces of 4-nitrophthalic acid mono-salt. The pH value of about 2.8 is obtained after addition of an amount of base slightly less than the equivalent amount, preferably about 90–95%, relative to the theoretical amount required for precipitating as mono-salt the whole of the 3-nitrophthalic acid present in the starting mixture. Optionally, the pH value can be raised to about 3.4 by the addition of further base to attain the amount theoretically required for precipitation of the residual 3-nitrophthalic acid in the form of mono-salt, and again a small amount of nitrophthalic acid mono-salt, consisting mainly of the 3-isomer, precipitates. This intermediate fraction can be either combined with the first fraction or subjected to a further separation process.

For precipitation of the remaining nitrophthalic acid, consisting predominantly of 4-nitrophthalic acid, in the form of a salt, the amount of base added is in itself not critical. Preferably, base is added in this stage until a pH value of about 4.5 is attained, or is added in an essentially stoichiometric amount, in order to be able to precipitate the whole of the residual nitrophthalic acid as mono-salt. The aqueous-organic reaction medium remaining after salt formation is completed can as a rule be used for further reactions directly without being processed. This is also possible when the base in this second stage is used in an amount less than the equivalent amount or in excess, and the reaction medium still contains residual nitrophthalic acid or unreacted base. It is merely to be ensured that, with the addition of a fresh starting isomeric mixture and if necessary of further base, the pH value of about 2.8 in the first reaction stage is not exceeded, and that the water content of the reaction medium is regulated if required.

The process according to the invention is therefore also well suited for continuous or semi-continuous operation.

The starting isomeric mixture has to be, as defined, free from organic residues, such as occur in the case of customary nitration of phthalic anhydride with concentrated nitric acid in the presence of concentrated sulfuric acid. The removal of acid residues of this kind can be effected in any chosen manner, advantageously by precipitation of the mineral acid salts by means of the addition of a suitable base. The removal of acid residues may also be performed—and with advantage—in the same reaction medium as that in which the stepwise precipitation according to the invention of the 3- and 4-nitrophthalic acid salts is performed, with preferably an alkali metal hydroxide or alkaline-earth metal hydroxide, particularly sodium hydroxide or potassium hydroxide, being used as base for the formation of the mineral acid salts. It is therefore possible to use in the process according to the invention, without the aid of additional apparatus and intermediate isolation, also crude nitrophthalic acid mixtures such as occur on nitration of phthalic anhydride, a factor which constitutes a significant simplification both technically and economically.

The conversion of the 3- and 4-nitrophthalic acid salts into the corresponding free acids is performed in a manner known per se, for example by treatment with aqueous inorganic acid, such as hydrochloric acid or sulfuric acid. If this conversion is carried out in the form of a recrystallisation, there are simultaneously removed also any traces present of the undesired isomer.

Any salt residues in the 3- or 4-nitrophthalic acid obtained can likewise be removed in the customary manner, for example by extraction of the 3- or 4-nitrophthalic acid with suitable inert organic solvents.

The 3- and 4-nitrophthalic acid can be obtained by the process according to the invention in a simple manner in pure, isomeric-free form and in good to very good yields. The reaction times are relatively short, the process can be performed under mild reaction conditions, and furthermore from an ecological point of view it is safe.

EXAMPLE 1

395 g of a crude moist nitrophthalic acid mixture [produced by nitration of 222.2 g (1.5 mols) of phthalic anhydride; ratio of 3-:4-nitrophthalic acid = approx. 48:52] is suspended in 1215 g of commercial methyl ethyl ketone in a 2.5-liter flask fitted with stirrer, reflux condenser, thermometer and pH-measuring electrode. To the mixture is added 90 g of water and the temperature is raised to 40° C. The clear yellowish solution formed shows a pH value of 0. There is then added with vigorous stirring an amount of 30% sodium hydroxide solution sufficient to bring the pH value of the mixture to 1.2. The aqueous crystal mass is subsequently separated, and the organic solution is put back into the same apparatus. After renewed heating to 40° C., 58.8 g (0.7 mol) of commercial sodium hydrogen carbonate is added portionwise with thorough stirring. After the evolution of $CO_2$ has subsided, the pH value of the mixture has risen to 2.8 and the mono-sodium salt of the 3-nitrophthalic acid precipitates in crystalline form. After cooling to 5° C., the salt is filtered off with suction, and dried at 80° C. until constant weight is obtained. The yield is 154.1 g of monosodium salt of 3-nitrophthalic acid (44.1% of theory, relative to phthalic anhydride used).

The mother liquor is again returned to the same apparatus and heated to 40° C. There is subsequently sprinkled in portionwise 67.2 g (0.8 mol) of sodium hydrogen carbonate, in the course of which the pH value of the mixture rises, after the evolution of $CO_2$ has subsided, to 4.5, and the monosodium salt of the 4-nitrophthalic acid precipitates in crystalline form. After cooling to 5° C., the salt is filtered off with suction, and dried at 80° C. until constant weight is obtained. The yield is 172.6 g of the monosodium salt of 4-nitrophthalic acid (54.5% of theory, relative to the phthalic anhydride used, still slightly contaminated by sodium hydrogen carbonate).

By treatment of the 3-nitrophthalic acid monosodium salt with 1000 g of 25% hydrochloric acid, there is obtained 131.2 g of crude isomer-free 3-nitrophthalic acid having a melting point of 207° C. (decomposition).

For the purpose of removing salt residues, 130 g of the crude 3-nitrophthalic acid obtained is taken up in 400 g of acetone. The reaction mixture is heated to reflux, filtered hot, and the solution obtained is evaporated to dryness to yield 123 g of pure isomer-free 3-nitrophthalic acid having a melting point of 213°-214° C. (decomposition). This corresponds to a yield of 39% of theory, relative to the employed phthalic anhydride.

In an analogous manner, the 4-nitrophthalic acid monosodium salt is converted, by treatment with 560 g of 25% hydrochloric acid, into 4-nitrophthalic acid. The yield is 157.6 g of crude isomer-free 4-nitrophthalic acid having a melting point of 162°-164° C. (decomposition). After processing as described above for the 3-nitrophthalic acid for removal of residual inorganic salts, there is obtained 123 g of pure isomer-free 4-nitrophthalic acid having a melting point of 172°-173° C. (decomposition). This corresponds to a yield of 39% of theory, relative to the phthalic anhydride used.

EXAMPLE 2

The procedure is carried out in the manner described in Example 1. After removal of the acid residues originating from the nitrating process, there is however added only 56.7 g (0.675 mol) of sodium hydrogen carbonate, as a result of which 149.9 g of 3-nitrophthalic acid monosodium salt is precipitated. After separation of this salt in the manner described in Example 1, a further 6.3 g (0.075 mol) of sodium hydrogen carbonate is added to the mother liquor, whereupon the pH value of the mixture rises to 3.4 and 10.7 g of a nitrophthalic acid monosodium salt mixture, consisting principally of the 3-isomer, is precipitated. This crystal fraction is likewise separated from the mother liquor and used in a subsequent separation process.

The monosodium salt of 4-nitrophthalic acid is subsequently precipitated from the mother liquor, as described in Example 1, by the addition of 63 g (0.75 mol) of sodium hydrogen carbonate, with 169.5 g being obtained.

By treatment of the two isomeric nitrophthalic acid monosodium salts with hydrochloric acid, in a manner analogous to that described in Example 1, there is obtained 126.1 g of crude isomer-free 3-nitrophthalic acid having a melting point of 209° C. (decomposition), and 154.3 g of crude isomer-free 4-nitrophthalic acid having a melting point of 164°–166° C. (decomposition). These two products still contain certain amounts of sodium chloride, from which they can be freed likewise in the manner described in Example 1.

EXAMPLE 3

211 g (1.0 mol) of a purified ¾-nitrophthalic acid mixture is placed into a 2.5-liter flask provided with stirrer, reflux condenser and thermometer. The isomer proportions in this mixture had been previously analytically determined as being 48.7 percent by weight of 3-nitrophthalic acid and 51.3 percent by weight of 4-nitrophthalic acid. To the mixture are added 840 g of commercial methyl ethyl ketone and 42 g of water. The temperature is raised to 35° C. with stirring, and a clear solution is formed. To this is added portionwise, within 15 minutes, 37.8 g (0.45 mol) of sodium hydrogen carbonate. After the evolution of $CO_2$ has subsided, stirring is continued for a further 15 minutes at 35° C., and the temperature is then lowered to 5° C. The sandy crystal sludge is filtered off with suction, and dried at 80° C. until constant weight is obtained. The yield is 110.1 g of beige-coloured powder (monosodium salt of 3-nitrophthalic acid).

The mother liquor is again returned to the described apparatus and is heated to 35° C. The 4-nitrophthalic acid monosodium salt is thereupon precipitated by the addition of 46.2 g (0.55 mol) of sodium hydrogen carbonate, likewise filtered off with suction and dried. The yield is 107.6 g of beige-coloured powder.

The monosodium salt of 3-nitrophthalic acid is subsequently recrystallised from 210 g of 15% hydrochloric acid, and the monosodium salt of 4-nitrophthalic acid from 140 g of 15% hydrochloric acid. Both products are then taken up each in 200 g of acetone, heated to reflux and filtered off from insoluble constituents, and the solutions are evaporated to dryness.

There are obtained in this manner 82.3 g of 3-nitrophthalic acid having a melting point of 216° C. (decomposition), corresponding to 80% of theory; and 78.8 g of 4-nitrophthalic acid having a melting point of 172°–173° C. (decomposition), corresponding to 74.8% of theory. Both products are pure according to thin-layer chromatography.

EXAMPLES 4–11

29.6 g (0.2 mol) of phthalic anhydride is nitrated by using the procedure described in Example 1. Removal of salt residues leaves 26 g of a purified 3-/4-nitrophthalic acid mixture. This is separated in the manner described in Example 1 into the isomers, and the 3- and 4-nitrophthalic acid salts obtained are then converted into the free acids, likewise as described in Example 1. The further reaction conditions and the yields of 3- and 4-nitrophthalic acid are summarised in the Table which follows.

TABLE

| Ex. No. | Solvent (200 g) | Base 4 or 3-nitro-phthalic acid monosalt | Base for 4-nitro-phthalic acid monosalt | Yield of 3-nitrophthalic acid (pure) (1) | Yield of 3-nitrophthalic acid (pure) (2) | Yield of 4-nitrophthalic acid (pure) (1) | Yield of 4-nitrophthalic acid (pure) (2) |
|---|---|---|---|---|---|---|---|
| 4 | ethyl alcohol | comm. sodium hydrogen carbonate 0.09 mol | comm. sodium hydrogen carbonate 0.11 mol | 37% | 42% | 28% | 32% |
| 5 | isopropyl alcohol | comm. sodium hydrogen carbonate 0.09 mol | comm. sodium hydrogen carbonate 0.11 mol | 35% | 39% | 26% | 30% |
| 6 | ethyl acetate | comm. sodium hydrogen carbonate 0.09 mol | comm. sodium hydrogen carbonate 0.11 mol | 38% | 43% | 32% | 36% |
| 7 | dioxane | comm. sodium hydrogen carbonate 0.09 mol | comm. sodium hydrogen carbonate 0.11 mol | 39% | 44% | 10% | 11% |
| 8 | ethylene glycol monomethyl ether | comm. sodium hydrogen carbonate 0.09 mol | comm. sodium hydrogen carbonate 0.11 mol | 35% | 39% | 25% | 28% |
| 9 | methyl ethyl ketone | potassium hydrogen carbonate 0.09 mol | potassium hydrogen carbonate 0.11 mol | 38% | 43% | 25% | 28% |
| 10 | methyl ethyl ketone | magnesium carbonate 0.09 mol | magnesium carbonate 0.11 mol | 35% | 39% | 20% | 23% |
| 11 | methyl ethyl ketone | calcium carbonate 0.09 mol | calcium carbonate 0.9 mol | 35% | 39% | 32% | 36% |

(1) % of theory, relative to phthalic anhydride used
(2) % of theory, relative to purified 3-/4-nitrophthalic acid mixture

What is claimed is:

1. A process for separating mixtures of 3- and 4-nitrophthalic acid, which process comprises treating a mixture of 3- and 4-nitrophthalic acid, which mixture is free from inorganic acid residues, in an aqueous-organic medium containing 1–20 percent by volume of water, at a temperature of between 20° and 100° C., stepwise with a base capable of forming salts of 3- and 4-nitrophthalic acid, which salts are essentially insoluble in the reaction medium, the treatment being carried out by adding base until a pH value of about 2.8 is obtained, separating the precipitating product consisting mainly of a 3-nitrophthalic acid mono-salt, subsequently precipitating, by the addition of further base, a product consisting principally of a 4-nitrophthalic acid salt, and finally converting the resulting nitrophthalic acid salts separately into the corresponding free acids.

2. A process according to claim 1, wherein the reaction is performed in an aqueous-organic medium which contains 5-10 percent by volume of water.

3. A process according to claim 1, wherein an inert polar organic solvent is used.

4. A process according to claim 1, wherein the organic solvent used is an aliphatic ketone, or an alkyl ester of aliphatic monocarboxylic acids having a total of 2-6 C atoms.

5. A process according to claim 1, wherein the organic solvent used is methyl ethyl ketone or ethyl acetate.

6. A process according to claim 1, wherein an inorganic base is used.

7. A process according to claim 1, wherein the base used is a hydroxide, carbonate or hydrogen carbonate of an alkali metal or alkaline-earth metal.

8. A process according to claim 1, wherein the base used is sodium hydrogen carbonate or potassium hydrogen carbonate.

9. A process according to claim 1, wherein the salt formation is performed at a temperature of between 30° and 50° C.

* * * * *